US007616321B2

(12) United States Patent
Korn

(10) Patent No.: US 7,616,321 B2
(45) Date of Patent: Nov. 10, 2009

(54) OPTICAL COUPLER FOR ROTATING CATHETER

(75) Inventor: Jeff Korn, Lexington, MA (US)

(73) Assignee: InfraReDx, Inc., Burlington, MA (US)

( * ) Notice: Subject to any disclaimer, the term of this patent is extended or adjusted under 35 U.S.C. 154(b) by 1184 days.

(21) Appl. No.: 10/615,279

(22) Filed: Jul. 8, 2003

(65) Prior Publication Data
US 2004/0109636 A1 Jun. 10, 2004

Related U.S. Application Data

(63) Continuation-in-part of application No. 10/309,477, filed on Dec. 4, 2002.

(51) Int. Cl.
*G01B 9/02* (2006.01)
(52) U.S. Cl. .................. 356/479; 356/477; 356/478; 356/497; 600/473; 600/476; 600/478
(58) Field of Classification Search .......... 600/407, 600/433, 434, 435, 437, 459, 466, 473, 477, 600/478, 160, 476–8
See application file for complete search history.

(56) References Cited

U.S. PATENT DOCUMENTS

| 6,134,003 | A  | * | 10/2000 | Tearney et al. | ............. 356/479 |
| 6,208,886 | B1 | * | 3/2001 | Alfano et al. | ............. 600/473 |
| 6,445,939 | B1 | * | 9/2002 | Swanson et al. | ............. 600/342 |
| 6,485,413 | B1 | * | 11/2002 | Boppart et al. | ............. 600/160 |
| 6,501,551 | B1 | * | 12/2002 | Tearney et al. | ............. 356/477 |
| 6,654,630 | B2 | * | 11/2003 | Zuluaga et al. | ............. 600/476 |
| 6,895,137 | B2 | * | 5/2005 | Zuluaga et al. | ............. 385/15 |
| 6,975,898 | B2 | * | 12/2005 | Seibel | ............. 600/473 |
| 2003/0125630 | A1 | * | 7/2003 | Furnish | ............. 600/461 |
| 2004/0111032 | A1 | * | 6/2004 | Korn | ............. 600/478 |

FOREIGN PATENT DOCUMENTS

| JP | 62028704 | 2/1987 |
| JP | 63201604 | 8/1988 |
| WO | WO02/088705 | 11/2002 |
| WO | WO03/104864 | 12/2003 |

OTHER PUBLICATIONS

Barber et al., "Ultrasonic Duplex Echo-Doppler Scanner," *IEEE Transactions on Biomedical Engineering*, vol. BME-21, No. 2, pp. 109-113 (Mar. 1974).

(Continued)

*Primary Examiner*—Brian Casler
*Assistant Examiner*—Baisakhi Roy
(74) *Attorney, Agent, or Firm*—Fish & Richardson, P.C.

(57) ABSTRACT

An optical coupler for coupling to a rotating catheter has a housing with a rotatable distal face and a stationary proximal face. The distal face has an eccentric port and a central port. A lens is disposed inside the housing to intercept a rotating collection beam emerging from the eccentric port and to re-direct the collection beam to a focus proximal to the lens as the collection beam rotates. A beam re-director disposed between the lens and the distal face is oriented to direct a delivery beam toward the central port.

16 Claims, 8 Drawing Sheets

OTHER PUBLICATIONS

Bow et al., "Cardiac Imaging with a Real-Time Ultrasonic Scanner of a Rotating Transducer Design," *Proceedings of The British Medical Ultrasound Society*, p. 645 (Aug. 1978).

"Coronary-Artery Bypass Surgery," *The Lancet*, pp. 264-265 (Feb. 4, 1978).

Hisanaga et al., "High Speed Rotating Scanner for Transesophageal Cross-Sectional Echocardiography," *The American Journal of Cardiology*, vol. 46, pp. 837-842 (Nov. 1980).

Lancée et al., "Construction of a circular ultrasonic array with miniature elements for cardiac application," Thorax Center, Department of Echocardiography and Central Research Workshop, Erasmus University, Rotterdam, The Netherlands, pp. 49-53 (undated).

Martin et al., "An Ultrasonic Catheter Tip Instrument for Measuring Volume Blood Flow," Departments of Anesthesiology & Bioengineering, University of Washington, Seattle, Washington, pp. 13-17 (undated).

Martin et al., "Ultrasonic Catheter Tip Instrument for Measurement of Vessel, Cross-Sectional Area," 27$^{th}$ ACEMB, Marriott Hotel, Philadelphia, Pennsylvania, p. 186 (Oct. 6-10, 1974).

Martin and Watkins, "An Ultrasonic Catheter for Intravascular Measurement of Blood Flow: Technical Details," *IEEE Transactions on Sonics and Ultrasonics*, vol. SU-27, No. 6, pp. 277-286 (Nov. 1980).

Pérez et al., "Applicability of Ultrasonic Tissue Characterization for Longitudinal Assessment and Differentiation of Calcification and Fibrosis in Cardiomyopathy," *American College of Cardiology*, vol. 4, No. 1, pp. 88-93 (Jul. 1984).

Tomoike et al., "Continuous measurement of coronary artery diameter in situ," *American Physiological Society*, pp. H73-H79 (undated).

Van Orden et al., "A technique for monitoring blood flow changes with miniaturized Doppler flow probes," *American Physiological Society*, pp. H1005-H1009 (undated).

Ycas and Barnes, "An Ultrasonic Drill for Cleaning Blood Vessels," Department of Electrical Engineering, University of Colorado, Boulder, Colorado, pp. 165-167 (undated).

* cited by examiner

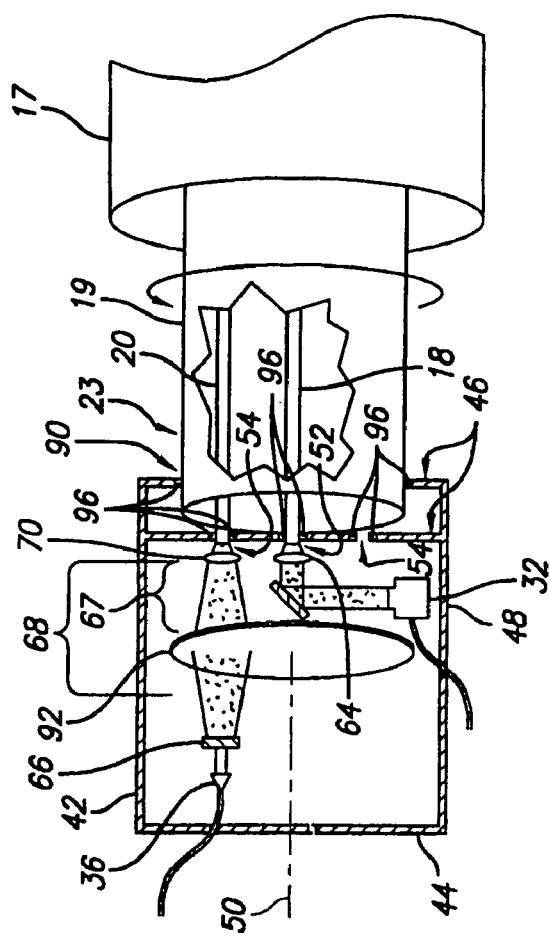
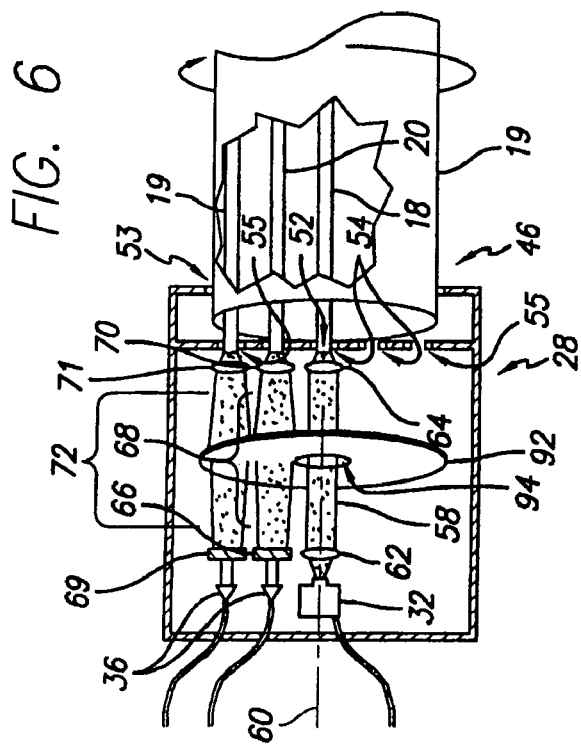

OPTICAL COUPLER FOR ROTATING CATHETER

RELATED APPLICATIONS

This application is a continuation-in-part of U.S. application Ser. No. 10/309,477, filed on Dec. 4, 2002, the contents of which are herein incorporated by reference.

TECHNICAL FIELD

This invention relates to fiber optic catheters, and more particularly to catheters that accommodate more than one optical fiber.

BACKGROUND

Vulnerable plaques are lipid filled cavities that form within the wall of a blood vessel. These plaques, when ruptured, can cause massive clotting in the vessel. The resultant clot can interfere with blood flow to the brain, resulting in a stroke, or with blood flow to the coronary vessels, resulting in a heart attack.

To locate vulnerable plaques, one inserts a catheter through the lumen of the vessel. The catheter includes a delivery fiber for illuminating a spot on the vessel wall and one or more collection fibers for collecting scattered light from corresponding collection spots on the vessel wall. The delivery fiber, and each of the collection fibers form distinct optical channels within the catheter. The catheter used for locating plaques is thus a multi-channel catheter.

In operation, a light source outside the catheter introduces light into the delivery fiber. A detector, also outside the catheter, detects light in the collection fiber and generates an electrical signal representative of that light. This signal is then digitized and provided to a processor for analysis.

A vulnerable plaque can be anywhere within the wall of the artery. As a result, it is desirable to circumferentially scan the illuminated spot and the collection spot around the vessel wall. One way to do this is to spin the multi-channel catheter about its axis. However, since neither the light source nor the processor spin with the catheter, it becomes more difficult to couple light into and out of the delivery and collection fibers while the catheter is spinning.

SUMMARY

The described device, method and system are based on the recognition that a lens can be made to focus light onto a fixed point even as the source of that light moves relative to the lens.

In one aspect, the invention includes an optical coupler having a housing with a rotatable distal face and a stationary proximal face. The distal face has an eccentric port and a central port. A lens is disposed inside the housing to intercept a rotating collection beam emerging from the eccentric port and to re-direct the collection beam to a focus proximal to the lens as the collection beam rotates. A beam re-director disposed between the lens and the distal face is oriented to direct a delivery beam toward the central port.

In some embodiments, the beam re-director is a pentaprism. However, other types of beam re-directors, for example a prism or a mirror, can also be used.

Certain embodiments also include a light source disposed to direct a delivery beam radially inward to the beam re-director, and/or a detector disposed at the focus for receiving the rotating collection beam.

In some embodiments, the lens is configured to focus the collection beam on an axis of rotation of the distal face. However, in other embodiments, the lens is configured to focus the collection beam off an axis of rotation of the distal face. In yet other embodiments, the lens is an axicon lens.

In another aspect, the invention includes a system for identifying vulnerable plaque. The system includes a rotating catheter having a collection fiber and a delivery fiber extending therethrough, and a housing with a rotatable distal face and a stationary proximal face. The distal face has an eccentric port and a central port. A lens is disposed inside the housing to intercept a rotating collection beam emerging from the eccentric port and to re-direct the collection beam to a focus proximal to the lens as the collection beam rotates. A beam re-director disposed between the lens and the distal face is oriented to direct a delivery beam toward the central port.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Embodiments of the invention may have one or more of the following advantages. By providing a continuous connection to both optical fibers, the rotary coupler permits the entire circumference of an artery to be scanned automatically.

A rotary coupler having the features of the invention can also be used to identify other structures outside but near a lumen, or on the surface of the lumen wall. For example cancerous growths within polyps can be identified by a catheter circumferentially scanning the lumen wall of the large intestine, cancerous tissue in the prostate may be identified by a catheter scanning the lumen wall of the urethra in the vicinity of the prostate gland, or Barrett's cells can be identified on the wall of the esophagus. In addition to its medical applications, the rotary coupler can be used in industrial applications to identify otherwise inaccessible structures outside pipes.

Other features and advantages of the invention will be apparent from the following detailed description, and from the claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 is a profile view of the multi-channel coupler incorporating additional fibers.

FIGS. 7-8 are embodiments that include a delivery beam re-director.

Like reference symbols in the various drawings indicate like elements.

DETAILED DESCRIPTION

System Overview

Figure 1:
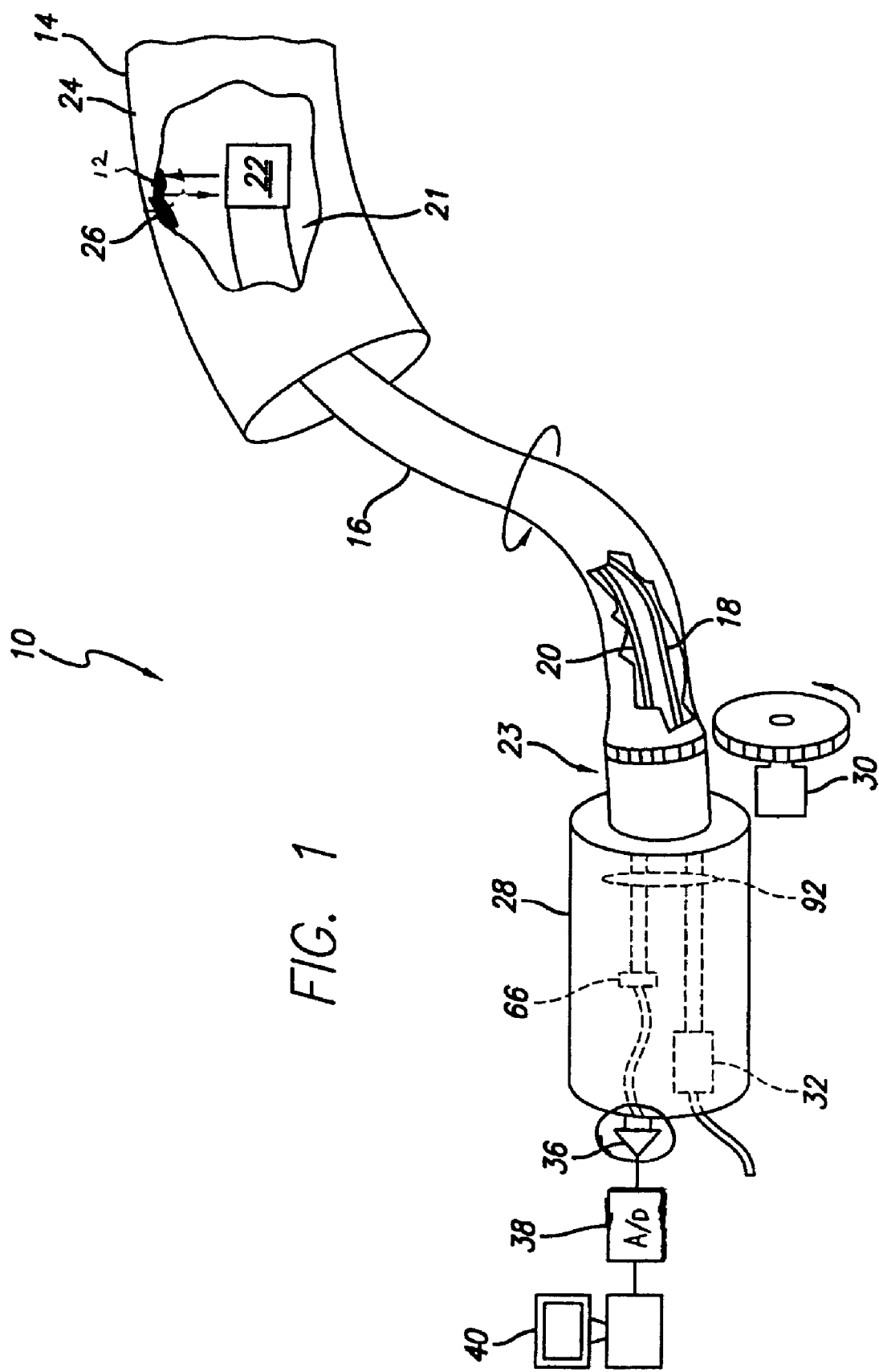
FIG. 1 is a system for identifying vulnerable plaque in a patient.

FIG. 1 shows a diagnostic system 10 for identifying vulnerable plaque 12 in an arterial wall 14 of a patient. The diagnostic system features a catheter 16 to be inserted into a selected artery, e.g. a coronary artery, of the patient. A delivery fiber 18 and a collection fiber 20 extend between a distal end 21 and a proximal end 23 of the catheter 16.

Figure 2:
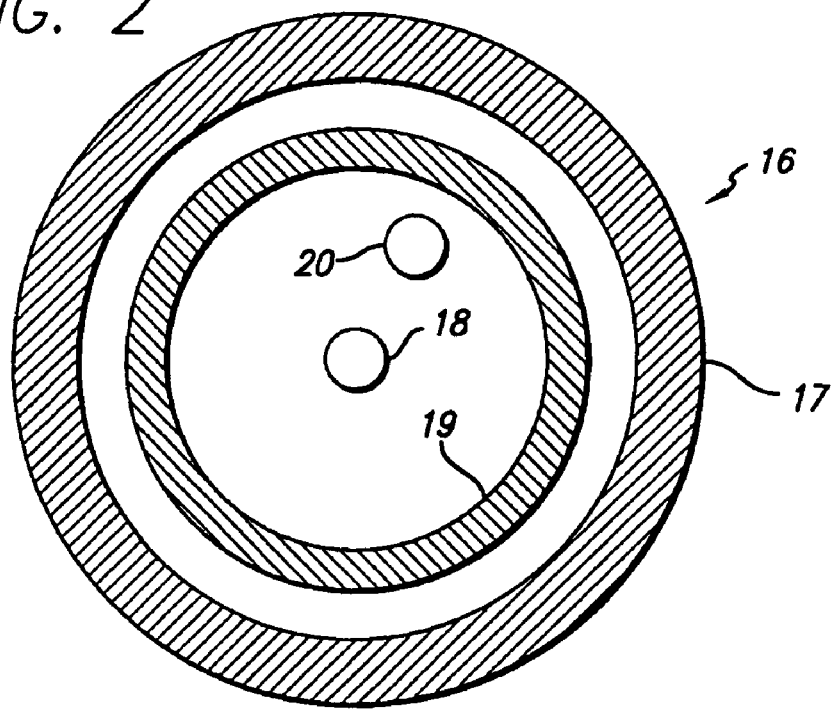
FIG. 2 is a cross-section of the multi-channel catheter in FIG. 1.

As shown in FIG. 2, the catheter 16 includes a jacket 17 surrounding a rotatable core 19. The delivery fiber 18 extends along the center of the core 19 and the collection fiber 20 extends parallel to, but radially displaced from, the delivery fiber 18. The rotatable core 19 spins at rate between approximately 4 revolutions per second and 30 revolutions per second.

Referring again to FIG. 1, at the distal end 21 of the catheter 16, a tip assembly 22 directs light traveling axially on the delivery fiber 18 toward an illumination spot 24 on the arterial wall 14. The tip assembly 22 also collects light from a collection spot 26 on the arterial wall 14 and directs that light into the collection fiber 20.

A multi-channel coupler 28, which is driven by a motor 30, engages the proximal end 23 of the catheter 16. The motor 30 spins the catheter 16, enabling the diagnostic system 10 to circumferentially scan the arterial wall 14 with the illumination spot 24.

The multi-channel coupler 28 guides a beam from a laser 32 (or other source, such as an LED, a super luminescent LED, or an arc lamp) into the delivery fiber 18 and guides light emerging from the collection fiber 20 into one or more detectors 66. The multi-channel coupler 28 performs these tasks while the catheter core 19 continuously spins.

The detectors provide an electrical signal indicative of light intensity to an amplifier 36 connected to an analog-to-digital ("A/D") converter 38. The A/D converter 38 converts this signal into data that can be analyzed by a processor 40 to identify the presence of a vulnerable plaque 12 hidden beneath the arterial wall 14.

Coupler Rotary Junction to Catheter

Figure 3:
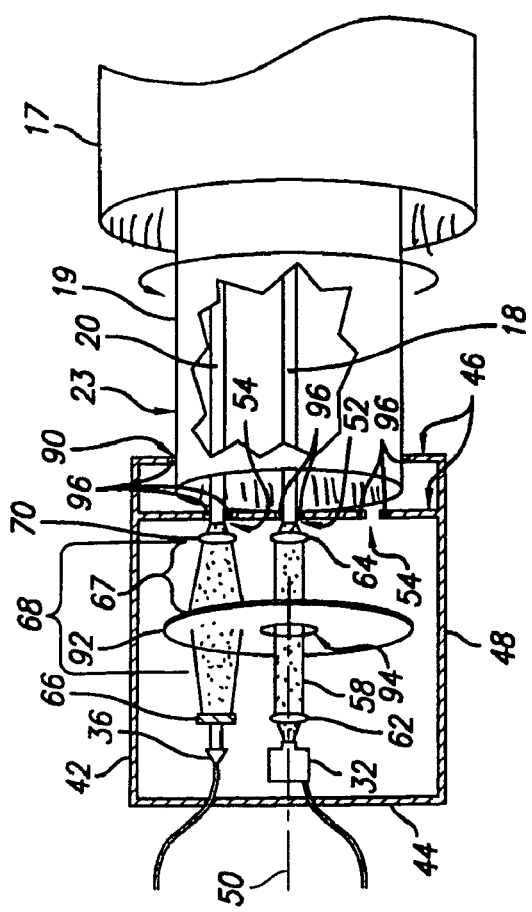
FIG. 3 is a profile view of the multi-channel coupler of FIG. 1.

A multi-channel coupler 28 for carrying out the foregoing tasks, as shown in FIG. 3, includes a cylindrical housing 42 having a proximal face 44 joined to a distal face 46 by a peripheral wall 48. The distal face 46 rotates with the catheter core 19, whereas the proximal face 44 and the remainder of the housing 42 remain stationary.

Figure 4:
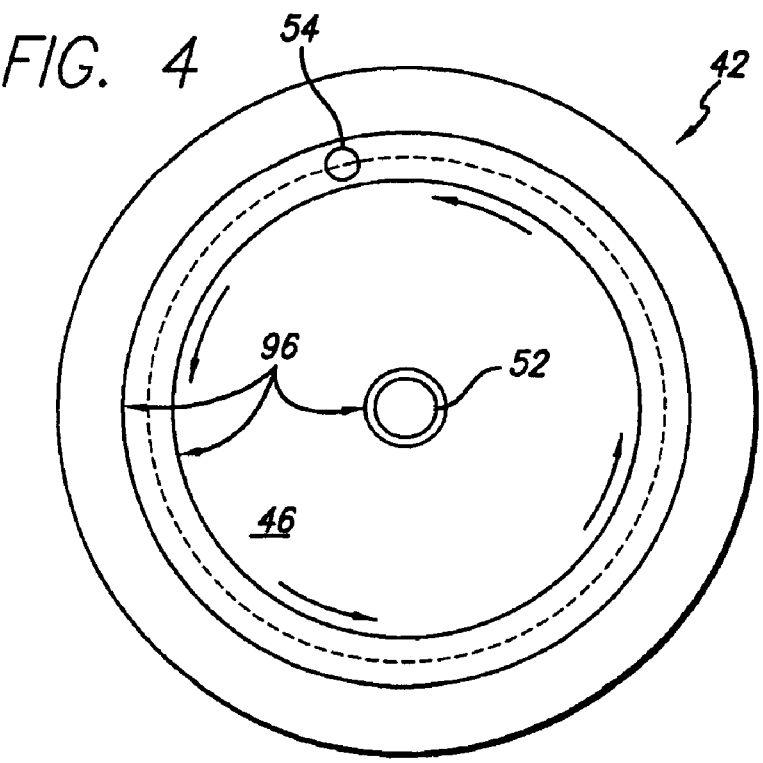
FIG. 4 is an end view of the multi-channel coupler of FIG. 1.

The distal face 46 of the housing 42 has a catheter core port 53 for receiving the catheter core 19, a central port 52 for receiving the delivery fiber 18, and an eccentric port 54 for receiving the collection fiber 20. The central port 52 is located at the intersection of an axis of rotation 50 with the distal face 46. The eccentric port 54 is radially displaced from the central port 52. As a result, when the catheter core 19 spins about the axis 50, the delivery fiber 18 remains stationary and the collection fiber 20 traces out a circular path, as shown in an end view in FIG. 4. Bearings 96 at the central port 52, eccentric port 54, and catheter core port 53 couple the housing 42 to the catheter core 19. The bearings 96 also enable the catheter core 19 to spin about the axis of rotation 50 that intersects the proximal and distal faces 44, 46 of the housing 42.

The distal face 46 of the housing 42 is rotatably coupled to the catheter 16. Two optical fibers extend through the catheter 16: a delivery fiber 18 for illuminating the arterial wall 14 and a collection fiber 20 that collects light scattered from the arterial wall 14. The catheter core 19 spins about the axis 50 while the housing 42 remains stationary.

A laser 32 directed towards the distal face 46 produces a delivery beam 58 centered on the axis 50 as shown in FIG. 3. A first collimating lens 62 collimates the delivery beam 58 and directs it through the housing 42 and through an aperture 94 of a rotation-to-stationary (R-S) lens 92. The R-S lens aperture 94 is a circular opening that is centered on the axis 50 and has a diameter slightly larger than the delivery beam 58. A first optical relay 64 within the housing 42 then receives the collimated delivery beam 58 and directs it distally across the housing 42 toward the central port 52, where it enters the delivery fiber 18. As used herein, an optical relay refers to a set of optical elements, such as lenses, prisms, and mirrors, arranged to direct light from a source to a destination.

In FIG. 3, this first optical relay 64 includes a converging lens focused at the central port 52. However, the first optical relay 64 can include components other than, or in addition to that shown in FIG. 3. Between the proximal face 44 and the central port 52, the delivery beam 58 is not constrained to travel along the axis 50 as shown in FIG. 3. The delivery beam 58 may travel on any path that leads to the delivery fiber 18. One design option, shown in FIG. 7, includes locating the laser 32 or directing the delivery beam 58 to start between the R-S lens 92 and the distal face 46. This would eliminate the need for the R-S lens aperture 94.

In the embodiment of FIG. 7, the light source 32 directs the delivery beam 58 radially toward a centrally mounted beam re-director 51. The beam re-director 51, which can be a prism, (including a penta-prism), or a mirror, re-directs the delivery beam 58 along the axis 50, toward the distal face 46. A first optical relay 64, disposed to intercept the delivery beam 58 on its way to the distal face 46, directs the delivery beam 58 into the delivery fiber 18.

A second optical relay 70 receives a collection beam 68 from the eccentric port 54 and directs it along a circular path that traverses a peripheral portion of the lens 92. The lens 92 brings the collection beam 68 to a focus at a detector 66, which generates an electrical signal in response thereto. This electrical signal is provided to the amplifier 36.

Figure 8:
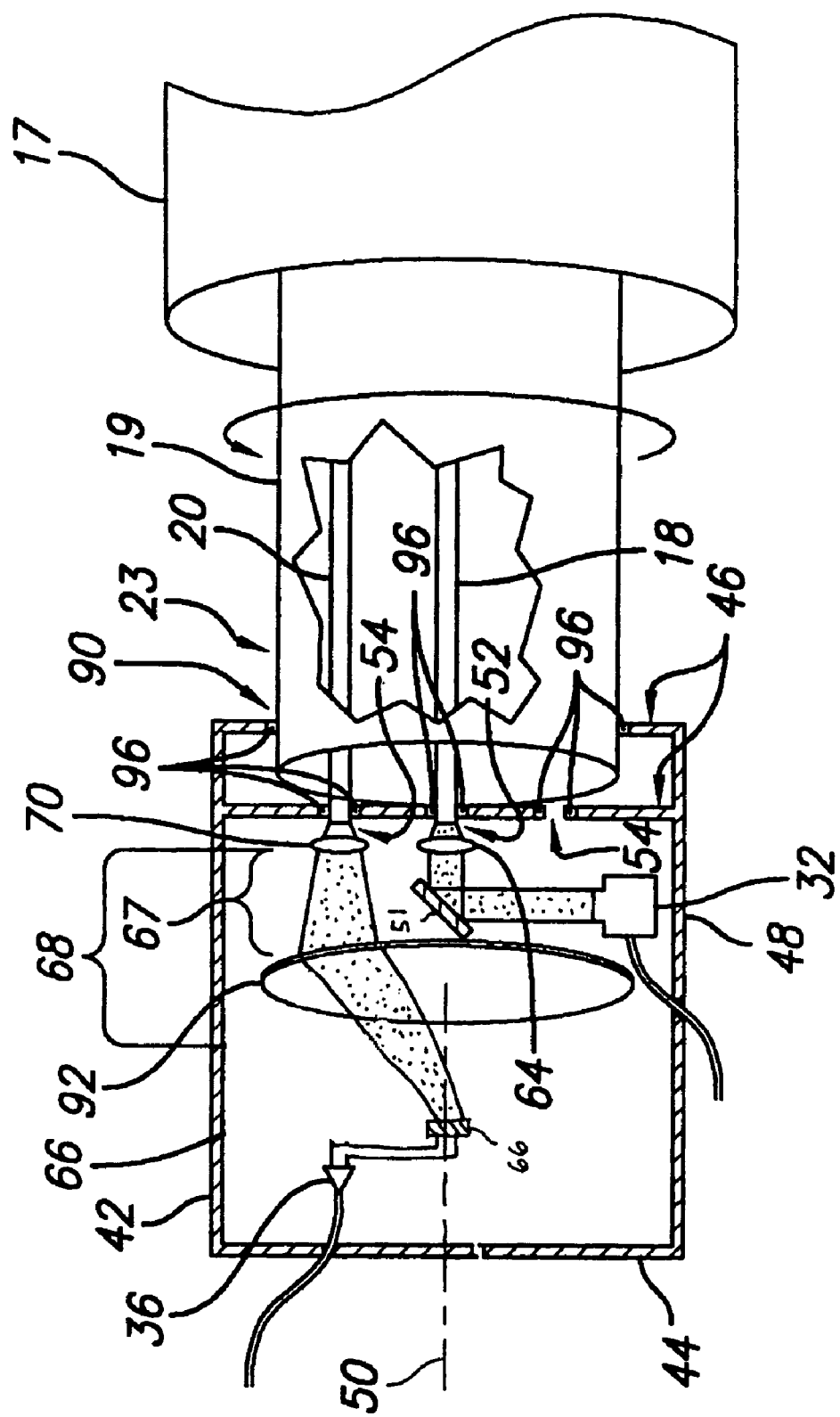
Figure 9:
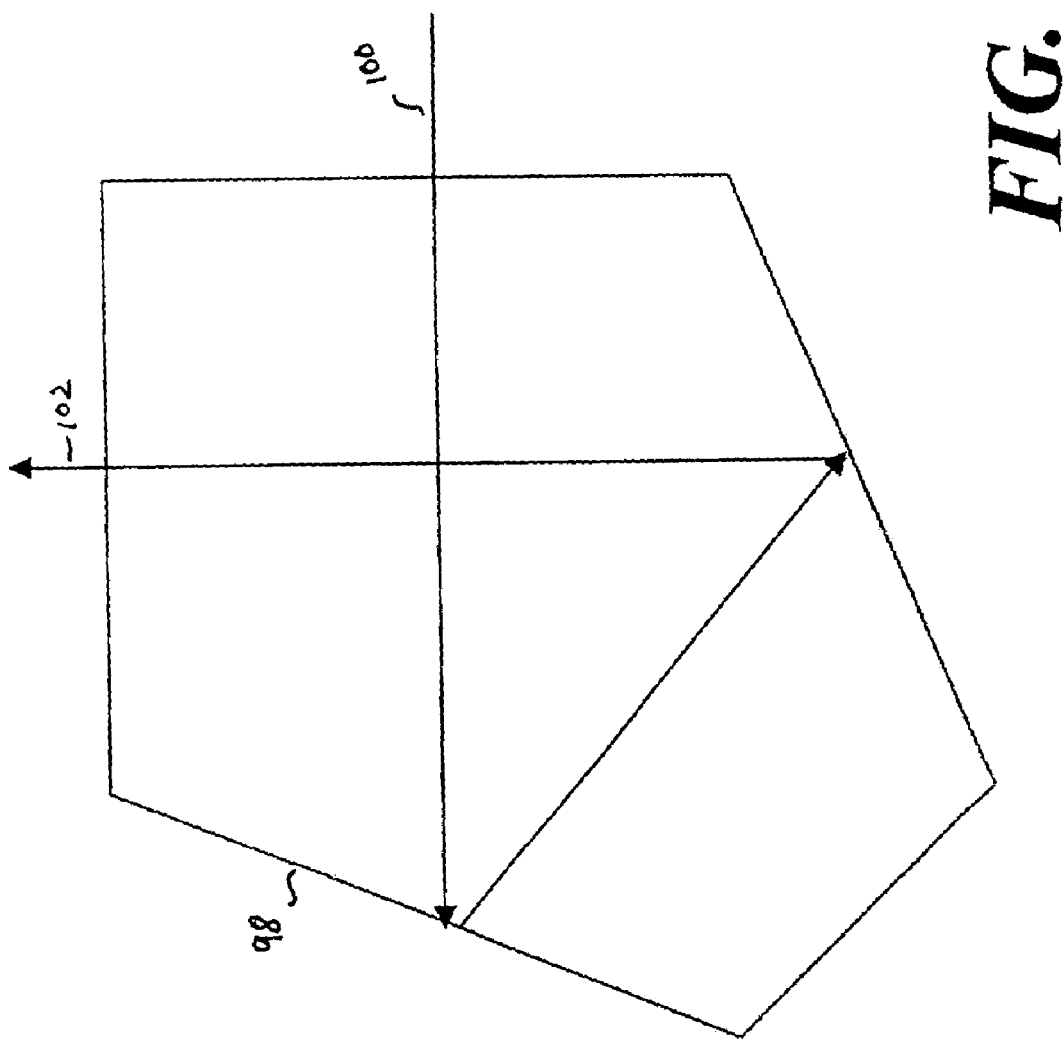
FIG. 9 is a penta-prism for use as a beam-redirector in the embodiments of FIGS. 7-8.

In FIG. 7, the detector 66 is disposed at a point offset from the axis 50. However, the lens 62 and the path traced by the collection beam 68 can be configured to direct the collection beam 68 toward the axis 50, as shown in FIG. 8. When this is the case, the detector 66 is placed on the axis 50, as shown in FIG. 8. A beam re-director 51 in the form of a penta-prism 98, shown in FIG. 9, is particularly useful because an input beam 100 incident on a penta-prism 98 always emerges as an output beam 102 orthogonal to the input beam 100. This property of a penta-prism 98 reduces the need for precision alignment.

The collection beam 67 is divided into a proximal side extending from the detector 66 to the R-S lens 92 and a distal side 67 extending from the R-S lens 92 to the eccentric port 54. A second optical relay 70 receives the collection beam 68 from the eccentric port 54 and directs it to the R-S lens 92. The R-S lens 92 directs the collection beam 68 to the detector 66 located towards the proximal face 44. The second optical relay 70 and the distal side of the collection beam 67 rotate circularly about the axis 50 and trace a circular path on the R-S lens 92. Without itself moving, the R-S lens 92 continuously redirects the collection beam 68 onto the stationary detector 66.

Figure 5:
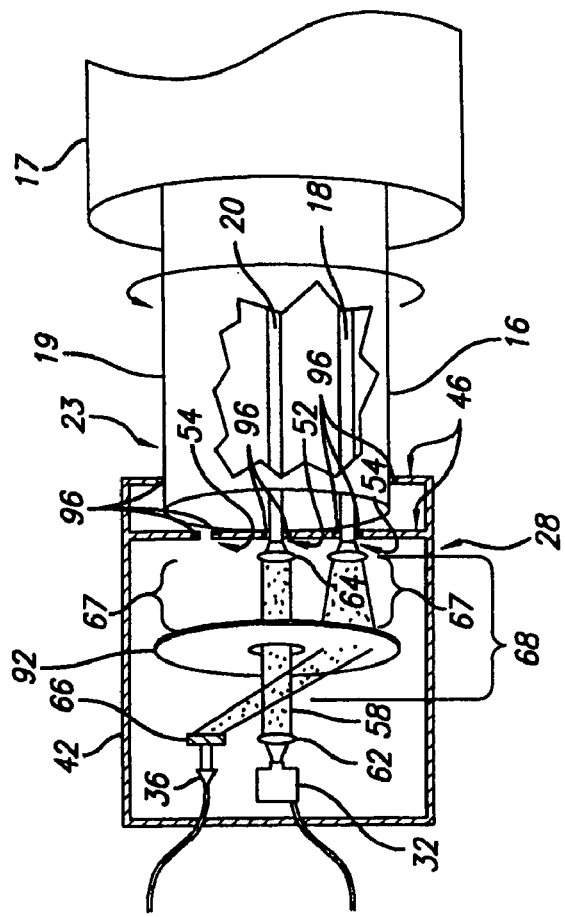
FIG. 5 is the same profile view of FIG. 3 with the core rotated 180 degrees.

In FIG. 5, the second optical relay 70 and the distal side of the collection beam 67 have rotated 180 degrees from the position depicted in FIG. 3. The R-S lens 92 directs the distal side of the collection beam 67, now located 180 degrees from its position in FIG. 3, back to the stationary detector 66 regardless of where the proximal side of the collection beam 67 intersects the R-S lens 92. The R-S lens 92 continuously directs the collection beam 68 onto the stationary detector 66 as the rotation of the core causes the optical relay and the distal side of the collection beam 67 to traverse a circular path on the R-S lens 92.

In one embodiment, the geometry or grading index of the R-S lens 92 is not symmetric about the axis 50. Instead, the geometry or grading index of the R-S lens 92 varies as a function of angle. For example, the portion of the lens through which the collection beam 68 passes in FIG. 3 refracts the collection beam 68 less than the portion of the lens through which the collection beam 68 passes in FIG. 5. As a result, the R-S lens 92 redirects the distal side of the collection beam 67 to the stationary detector 66 even as the proximal side of the collection beam 67 traces a circular path on R-S lens 92. The R-S lens 92 can include a variety of optical elements, such as lenses, prisms, and mirrors, arranged to direct light from a rotating source to a fixed destination. A central portion of the lens can be removed or made transparent to allow the delivery beam 58 to pass unaltered. A peripheral portion of the R-S lens 92 can be reduced to only the portion of the lens through which the collection beam 68 passes, thereby forming a donut shaped lens. This donut shaped lens would reduce the material needed to produce the R-S lens 92.

Figure 10:
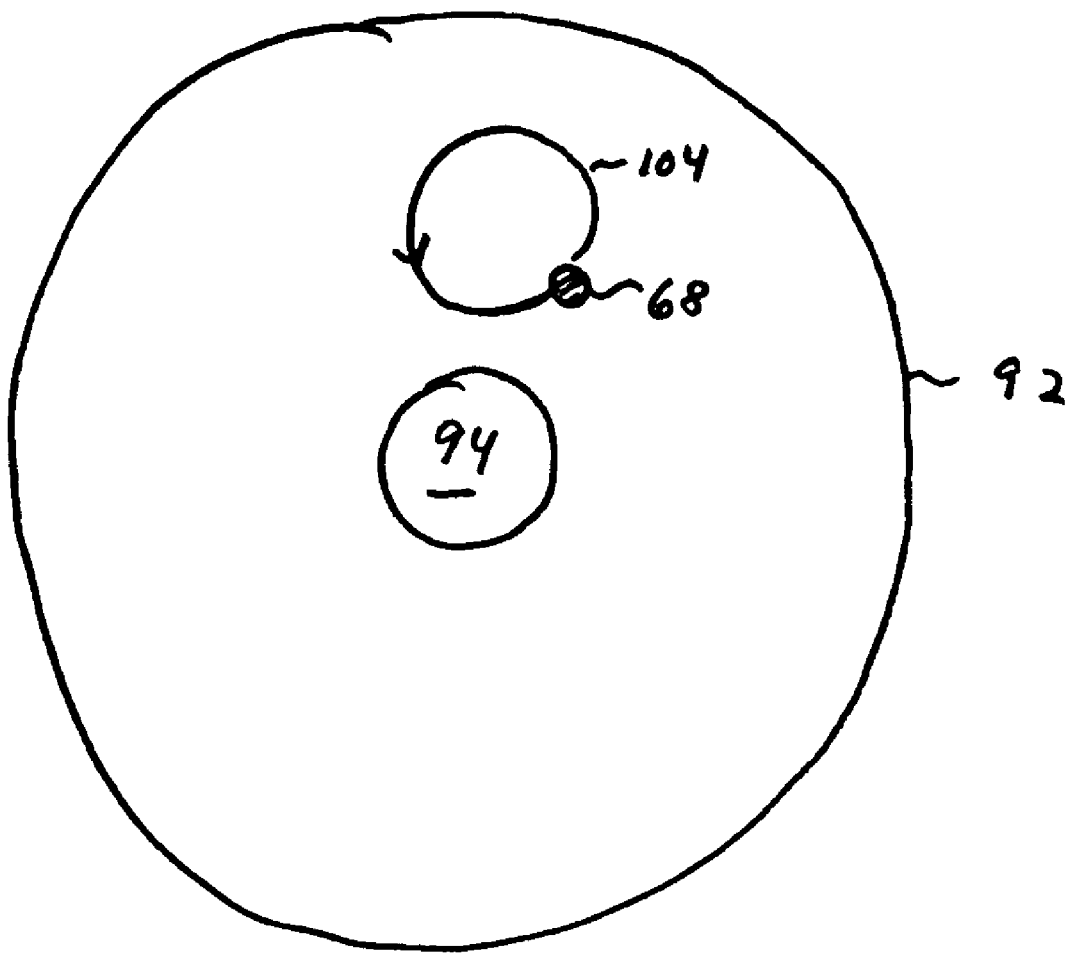
FIG. 10 is a schematic view of a path traced by a collection beam on a lens.
Figure 11:
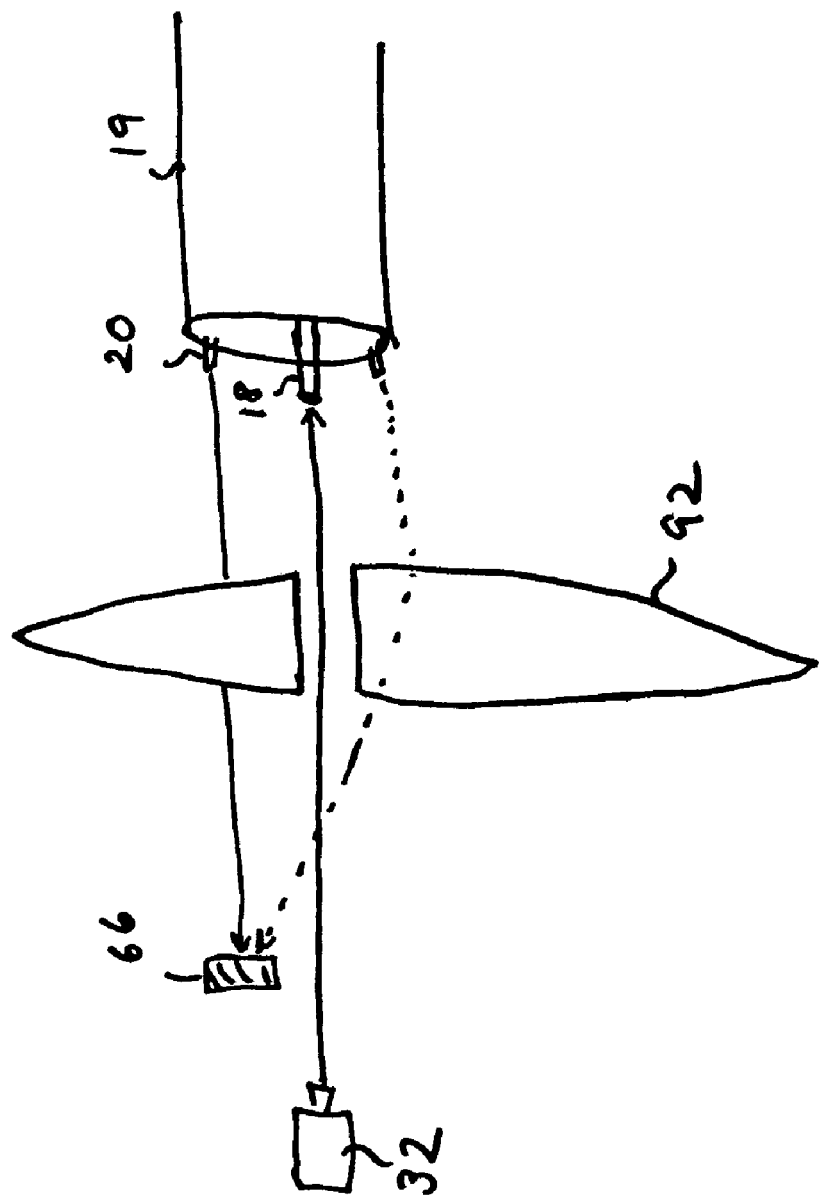
FIG. 11 is a schematic view of a catheter core whose axis of rotation is offset from the axis of the lens.

In another embodiment, the R-S lens 92 is symmetric about the axis 50, however the center of a circular path 104 traced out by the collection beam 68 is offset from the axis 50, as shown in FIG. 10. This can be achieved, for example, by offsetting the lens 92 relative to the catheter core 19 as shown in FIG. 11. Note that in this embodiment, as well as in the embodiment of FIG. 3, the collection beam 68 traverses a path through portions of a 92 lens having different optical characteristics, the difference being that in FIG. 3, the lens 92 is radially asymmetric and the axis of rotation 50 is coincident with the center of the lens 92, whereas in FIG. 7, the lens 92 is radially symmetric, but the axis of rotation 50 is offset from the center of the lens.

In another embodiment, the R-S lens 92 is an axicon lens, also known as a conical lens, or a rotationally symmetric prism. Such lenses cause the collection beam 68 to pass through the same location regardless of the angle of the collection fiber 20 and to do so without focusing the collection beam 68.

Other Embodiments

The optical couplers shown in FIGS. 1-5 are two-channel couplers. Each has a delivery channel that carries the delivery beam 58 and a collection channel for carrying a collection beam 68. However, additional collection or delivery channels can be added by providing additional collection ports or delivery ports, each of which is in communication with an additional collection fiber or delivery fiber.

In the embodiment of FIG. 6, an additional eccentric port 55 and optical relay 71 are provided in the distal face 46. The collection beams 68 and 72 emerging from the apertures and relays form concentric nested traces on the R-S lens 92. The R-S lens 92 then directs these traces to their perspective stationary detectors 66 and 69. Analogous to the depiction and discussion of FIGS. 3 and 5, the R-S lens continuously directs the collection beams 68 and 72 onto the stationary detectors 66 and 69 as the optical relays 70 and 71 and the distal side of the collection beams rotate from 0 to 360 degrees in a circular path. This embodiment is not limited to a single additional collection beam. The embodiment would include the capacity to handle a plurality of additional collection fibers. In addition, the embodiment is not limited to only additional collection fibers. Additional delivery fibers could also be present.

All lenses and optical relays referred to herein are shown as having a single optical element. However, each of these structures can include two or more optical elements in optical communication with each other.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An optical coupler comprising:
   a housing with a rotatable distal face and a stationary proximal face, the distal face having an eccentric port and a central port;
   a lens disposed inside the housing to intercept a rotating collection beam emerging from the eccentric port and to re-direct the collection beam to a focus proximal to the lens as the collection beam rotates; and
   a beam re-director disposed between the lens and the distal face, the beam re-director being oriented to direct a delivery beam toward the central port.

2. The optical coupler of claim 1, further comprising a light source disposed to direct a delivery beam radially inward to the beam re-director.

3. The optical coupler of claim 1, wherein the beam re-director comprises a penta-prism.

4. The optical coupler of claim 1, wherein the beam re-director comprises a prism.

5. The optical coupler of claim 1, wherein the beam re-director comprises a mirror.

6. The optical coupler of claim 1, further comprising a detector disposed at the focus for receiving the rotating collection beam.

7. The optical coupler of claim 1, wherein the lens is configured to focus the collection beam on an axis of rotation of the distal face.

8. The optical coupler of claim 1, wherein the lens is configured to focus the collection beam off an axis of rotation of the distal face.

9. The optical coupler of claim 1, wherein the lens comprises an axicon lens.

10. A system for identifying vulnerable plaque, the system comprising:
    a rotating catheter having a collection fiber and a delivery fiber extending therethrough;
    a housing with a rotatable distal face and a stationary proximal face, the distal face having an eccentric port and a central port;
    a lens disposed inside the housing to intercept a rotating collection beam emerging from the eccentric port and to re-direct the collection beam to a focus proximal to the lens as the collection beam rotates; and a beam re-director disposed between the lens and the distal face, the beam re-director being oriented to direct a delivery beam toward the central port.

11. The system of claim 10, further comprising a light source disposed to direct a delivery beam radially inward to the beam re-director.

12. The system of claim 10, wherein the beam re-director comprises a penta-prism.

13. The system of claim 10, wherein the beam re-director comprises a prism.

14. The system of claim 10, wherein the beam re-director comprises a mirror.

15. The system of claim 10, further comprising a detector disposed at the focus for receiving the rotating collection beam.

16. The system of claim 10, wherein the lens comprises an axicon lens.

* * * * *

UNITED STATES PATENT AND TRADEMARK OFFICE
CERTIFICATE OF CORRECTION

| | | |
|---|---|---|
| PATENT NO. | : 7,616,321 B2 | Page 1 of 1 |
| APPLICATION NO. | : 10/615279 | |
| DATED | : November 10, 2009 | |
| INVENTOR(S) | : Jeff Korn | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this
Eleventh Day of January, 2011

David J. Kappos
*Director of the United States Patent and Trademark Office*